US008926094B2

(12) United States Patent  (10) Patent No.: US 8,926,094 B2
Pirie  (45) Date of Patent: Jan. 6, 2015

(54) IMAGING ADAPTOR FOR CAMERA

(75) Inventor: Christopher Pirie, Upton, MA (US)

(73) Assignee: Tufts University, Medford, MA (US)

( * ) Notice: Subject to any disclaimer, the term of this patent is extended or adjusted under 35 U.S.C. 154(b) by 44 days.

(21) Appl. No.: 13/825,578

(22) PCT Filed: Sep. 13, 2011

(86) PCT No.: PCT/US2011/051352
§ 371 (c)(1),
(2), (4) Date: Jun. 6, 2013

(87) PCT Pub. No.: WO2012/039998
PCT Pub. Date: Mar. 29, 2012

(65) Prior Publication Data
US 2013/0258281 A1 Oct. 3, 2013

Related U.S. Application Data

(60) Provisional application No. 61/386,128, filed on Sep. 24, 2010.

(51) Int. Cl.
A61B 3/14 (2006.01)
A61B 3/10 (2006.01)
A61B 3/02 (2006.01)

(52) U.S. Cl.
USPC .......................... 351/206; 351/205; 351/233

(58) Field of Classification Search
USPC ................................................ 351/200–246
See application file for complete search history.

(56) References Cited

U.S. PATENT DOCUMENTS

2007/0159600 A1* 7/2007 Gil et al. ....................... 351/221
2009/0167933 A1* 7/2009 Miura et al. .................. 348/369
2010/0214402 A1* 8/2010 Schute et al. .................. 348/77

FOREIGN PATENT DOCUMENTS

| GB | 2359375 | 8/2001 |
| WO | 03/094706 | 11/2003 |
| WO | 2006/016366 | 2/2006 |
| WO | 2009/092598 | 7/2009 |

* cited by examiner

Primary Examiner — Mohammed Hasan
(74) Attorney, Agent, or Firm — Occhiuti & Rohlicek LLP

(57) ABSTRACT

An adaptor adapts an SLR camera for use as an ophthalmic viewing and imaging device. The adaptor is mounted to the camera between the camera body and the camera lens, and includes optical components arranged to direct illumination of the interior of the eye. The adaptor includes a first light source configured to provide a maximum level of illumination that is sufficient to identify structures of interest within an interior of an eye. The adaptor directs light from a second, external source to provide a level of illumination sufficient to obtain a fundus image. Optical components within the adaptor define a first optical pathway for directing light from the first light source to the lens, a second optical pathway for directing light from the second light source to the camera lens, and a third optical pathway for directing light from the camera lens through the adaptor to the camera.

29 Claims, 9 Drawing Sheets

IMAGING ADAPTOR FOR CAMERA

CROSS-REFERENCE TO RELATED APPLICATIONS

This application is a National Stage of International application no. PCT/US2011/051352 filed on Sep. 13, 2011, which claims priority to U.S. provisional application No. 61/386,128, filed on Sep. 24, 2010, the contents of which are hereby incorporated by reference in their entirety.

BACKGROUND OF THE INVENTION

Fundus evaluation and its benefits have long been known in both physician based and veterinary medicine. Fundus photography is a tool used for such evaluation, and is often used to document the healthy eye as well as abnormalities such as lesions and their progression over time. In addition, fundus photography may be used for teaching purposes. Furthermore, as is particularly true in physician based medicine, fundus photographic documentation is invaluable in legal proceedings.

SUMMARY

In some aspects, an adaptor is provided that is configured to adapt a camera for use as an ophthalmic viewing and imaging device. The adaptor includes a body including a first interface configured to connect to the camera so that an optical axis of the adaptor is aligned with an optical axis of the camera and a second interface configured to connect to a camera lens so that the optical axis of the adaptor is aligned with an optical axis of the camera lens. The adaptor includes a first light source disposed within the body and configured to provide a level of illumination that is, at maximum, sufficient to identify structures of interest within an interior of an eye. The adaptor further includes a first optical pathway for directing light from the first light source to the camera lens, a second optical pathway for directing light from a second light source to the camera lens, the second light source disposed externally relative to the body, and a third optical pathway for directing light from the camera lens through the adaptor to the camera.

In some aspects, an ophthalmic viewing and imaging device is provided. The device includes a camera including a camera lens, and an adaptor connected to the camera so as to be disposed between the camera and the camera lens. The adaptor includes a body including a first interface configured to connect to the camera so that an optical axis of the adaptor is aligned with an optical axis of the camera and a second interface configured to connect to the camera lens so that the optical axis of the adaptor is aligned with an optical axis of the camera lens. The adaptor includes a first light source configured to provide a level of illumination that is, at maximum, sufficient to identify structures of interest within an interior of an eye. In addition, the adaptor includes a first optical pathway for directing light from the first light source to the camera lens, a second optical pathway for directing light from a second light source to the camera lens, and a third optical pathway for directing light from the camera lens through the adaptor to the camera.

The adaptor and ophthalmic imaging and viewing device may include one or more of the following features: The first, second and third optical pathways each include a portion that is coincident with the optical axis of the camera. The first light source includes a light emitting diode. The device further comprises the second light source, the second light source configured to provide a level of illumination that is, at minimum, sufficient to obtain images of the structures of interest. The second light source includes a flash. The second light source includes a camera flash. The second light source is configured to correspond to a guide number of at least 20 in feet at an ISO of 100. The adaptor is configured to permit selective insertion and removal of a band pass filter. The adaptor further includes a band pass filter disposed in the second optical pathway. The band pass filter is configured to transmit light having a wavelength in a range of 485 nm to 500 nm. The band pass filter is configured to transmit light having a wavelength in a range of 770 nm to 810 nm.

The adaptor and ophthalmic imaging and viewing device may include one or more of the following additional features: The first optical pathway includes the first light source, a first beam splitter which directs a portion of the light emitted from the first light source to a second beam splitter, and the second beam splitter which directs a portion of the light received from the first beam splitter along the optical axis of the adapter in a direction toward the second interface. The first beam splitter is a 30R/70T beam splitter. The second beam splitter is a 50R/50T beam splitter. The adaptor further includes a polarized filter disposed in the first optical pathway between the first and second beam splitters. The third optical pathway includes a second polarizing filter, the second polarizing filter having an opposed orientation relative to the polarizing filter of the first optical pathway. The adaptor further includes a mirror disposed so as to deflect light transmitted through the second beam splitter in a direction away from the first interface. The third optical pathway includes the second beam splitter.

The adaptor and ophthalmic imaging and viewing device may include one or more of the following additional features: The second optical pathway includes a mirror which directs light emitted from the second light source toward a beam splitter, and a beam splitter which directs a portion of the light received from the mirror along the optical axis of the adapter in a direction toward the second interface. The beam splitter is a 50R/50T beam splitter. The adaptor further includes a polarized filter disposed in the second optical pathway between the mirror and the beam splitter. The third optical pathway extends along the optical axis, and passes through each of the first and second interfaces. The third optical pathway includes a band pass filter disposed between a polarizing filter and the first interface. The band pass filter is configured to transmit light having a wavelength in a range of 520 nm to 630 nm. The third optical pathway includes a lens disposed between the band pass filter and the first interface. The body includes a cylindrical base having longitudinal axis coincident with the optical axis of the adaptor, and a tube extending outward from a surface of the base and along an axis transverse to the optical axis of the adaptor. The tube can be replaced.

The viewing and imaging device may further include one or more of the following features: The device further includes a lens mounted to the camera lens on a side of the camera lens that is opposed to the adaptor. The third optical pathway includes a band pass filter disposed between the first interface and the camera image detector. The band pass filter is configured to transmit light having a wavelength in a range of 820 nm to 850 nm.

In some aspects, a method of viewing and imaging of the fundus of an eye is provided. The method includes the following method steps: Providing a camera having a camera lens and providing a flash. Securing an adaptor to the camera, where the adaptor includes a body including a first interface configured to connect to the camera so that an optical axis of the adaptor is aligned with an optical axis of the camera and a second interface configured to connect to the camera lens so that the optical axis of the adaptor is aligned with an optical axis of the camera lens, a first light source configured to provide a level of illumination that is, at maximum, sufficient to identify structures of interest within an interior of the eye, a first optical pathway for directing light from the first light source to the lens, a second optical pathway for directing light from the flash to the camera lens, and a third optical pathway for directing light from the camera lens through the adaptor to the camera. Securing the camera lens to the second interface of the adaptor to obtain a viewing and imaging device. Viewing the fundus through the device to identify structures of interest; and imaging the fundus by actuating the camera including the camera flash.

The method may include one or more of the following features: The device further includes a first band pass filter disposed in the second optical pathway and configured to transmit light having a wavelength of in a range of 485 nm to 500 nm, and a second band pass filter disposed in the third optical pathway and configured to transmit a wavelength in a range of 520 nm to 630 nm, and the imaging step includes fluorescein imaging. The device further includes a first band pass filter disposed in the second optical pathway and configured to transmit light having a wavelength in a range of 770 nm to 810 nm, and a second band pass filter disposed in the third optical pathway and configured to transmit a wavelength in a range of 820 nm to 850 nm, and the imaging step includes indocyanine imaging.

The adaptor disclosed herein can advantageously be used with a conventional digital Single Lens Reflex (SLR) camera to provide an eye image viewing and acquisition device. The adaptor is easy to install and use. Its use is not limited to one particular brand or model of SLR camera body or lenses.

Since the adaptor can be used with any conventional SLR camera, the resulting imaging and viewing device provides excellent image acquisition using true co-axial illumination with very high resolution relative to some conventional digital fundus cameras. For example, when the adaptor is used with the Canon Rebel® XTi digital SLR (dSLR), the resulting images have an effective pixel count of 10.1 megapixels. In addition, since the adaptor can be used with any conventional dSLR camera, the resolution is easily improved by replacing the camera with a camera of higher resolution. This resolution can be compared with some conventional dedicated digital fundus cameras that provide images having a resolution in a range between 1.5-2 megapixels. As such, the image quality provided by these conventional devices often significantly lag behind the capabilities of currently available dSLR cameras.

Further advantageously, the compact size and light weight of the device allows it to be easily handled and transported to remote locations (i.e. bed side evaluation, remote satellite clinic).

Because the adaptor is used with a conventional dSLR camera, the resulting viewing and imaging device provides versatility including the ability to control exposure via changes in shutter speed, aperture, and ISO settings.

The imaging and viewing device can be further improved by use of the indirect ophthalmic lens, which permits further control over the field of view and magnification, thereby allowing the examiner more detailed documentation, if necessary. As these lenses are common to the examiner (i.e. ophthalmologist), this alteration is simple and does not contribute to additional costs.

When combined with some conventional dSLR cameras having video imaging capabilities of such dSLR cameras, the adaptor additionally permits acquisition of video image recording. Furthermore, no specialized software or image editing programs are required.

A still further advantage of the disclosed viewing and imaging device is that it allows for the easy insertion of bandpass (interference) filters, thereby providing the examiner an option for fluorescein and/or indocyanine green angiography studies.

In addition, the eye imaging and viewing device obtained by mounting the adaptor to the dSLR camera provides images of the interior surface of the eye at a relative low cost. For example, some conventional dedicated digital fundus cameras are cost prohibitive. This is particularly true in veterinary medicine applications since the cost to purchase a conventional dedicated digital fundus camera can range between 40,000 to 60,000 US dollars or more. Thus, when used in combination with a conventional dSLR camera, the adaptor can be provided for approximately one fortieth the cost of some conventional digital fundus imaging cameras, while maintaining high quality images, and improving versatility and portability.

Illumination of the image is performed via a small LED, however, image exposure is controlled by the flash unit of the camera body itself (or an accessory flash unit). This illumination system offers a great advantage over previous designs, as exposure and flash settings are still dependent and controlled by the TTL (through the lens) metering system. Additionally, the ability to utilize an accessory flash (if desired) allows for even greater variability, as one may reduce the recycling time of the flash, thereby increasing the number of images collected in a rapid sequence, a feature that is important for fluorescein and/or indocyanine green angiography.

Placement of the adaptor is between the body and lens, resulting in forward displacement of the camera lens relative to the camera body. This creates a shorter working distance between the examiner and the patient while increasing image magnification.

Additionally, when used, the indirect ophthalmic lens is mounted on the camera lens, providing a virtual image (upright image) and improving usability of the system. Alternatively, axial movement of the indirect ophthalmic lens along the optical axis of the system may be performed, such that its focal point is located at the focal point of the camera lens. This configuration would provide a real image (upside down and reversed), a view common to ophthalmologists. Also, as the indirect ophthalmic lens is independent of the adaptor, use of the eye viewing and imaging device is not limited to fundus imaging. For example, removal of the indirect lens provides coaxial illumination during close up and macrophotography work. Furthermore, placement of the adaptor between the camera and lens results in a solid construction and there are no moving external components.

DETAILED DESCRIPTION

Figure 1:
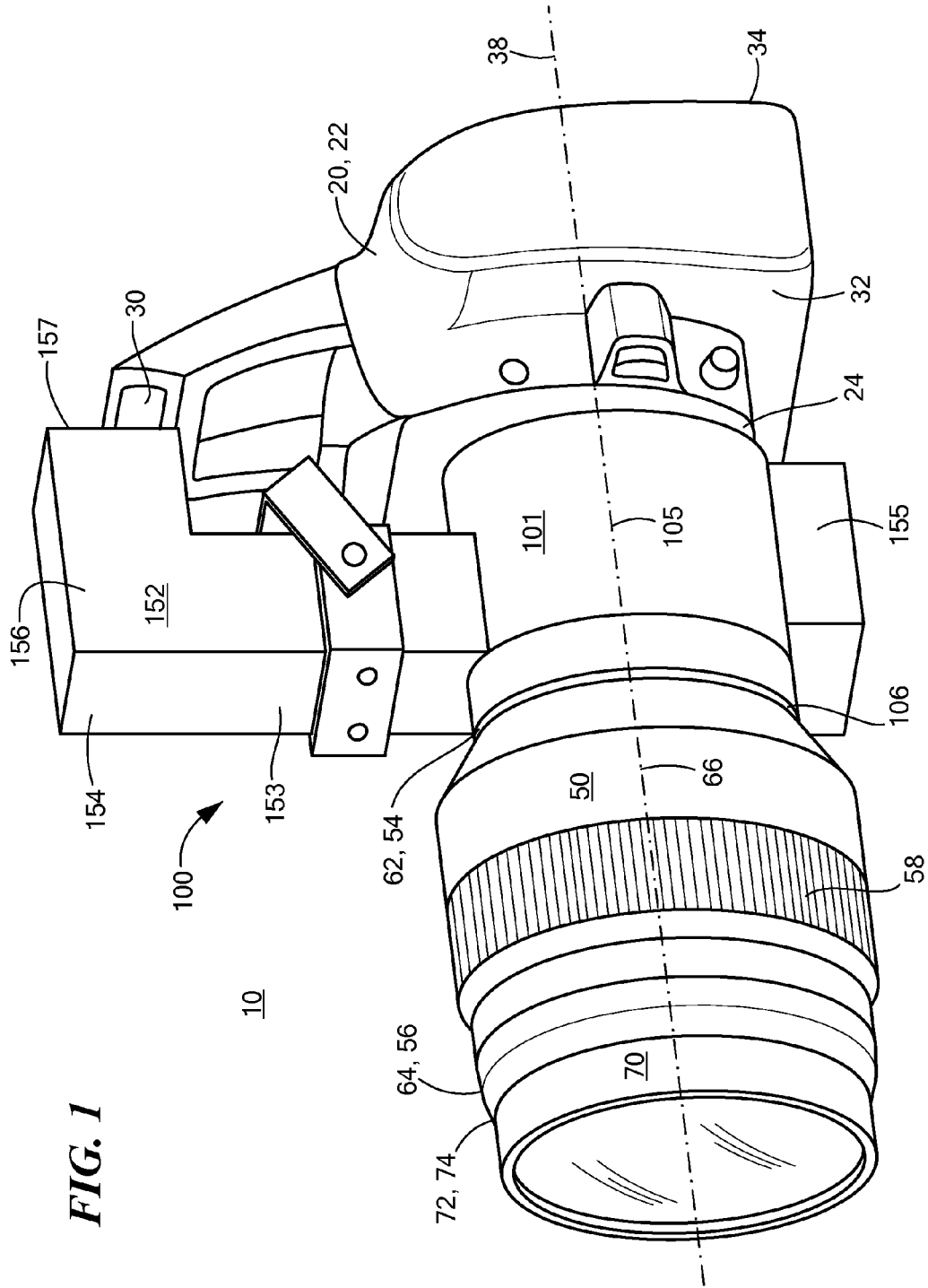
FIG. 1 is a perspective view of an ophthalmic viewing and imaging device including a camera, a camera lens, an adaptor disposed between the camera and camera lens, and an indirect ophthalmic lens secured to the camera lens.
Figure 2:
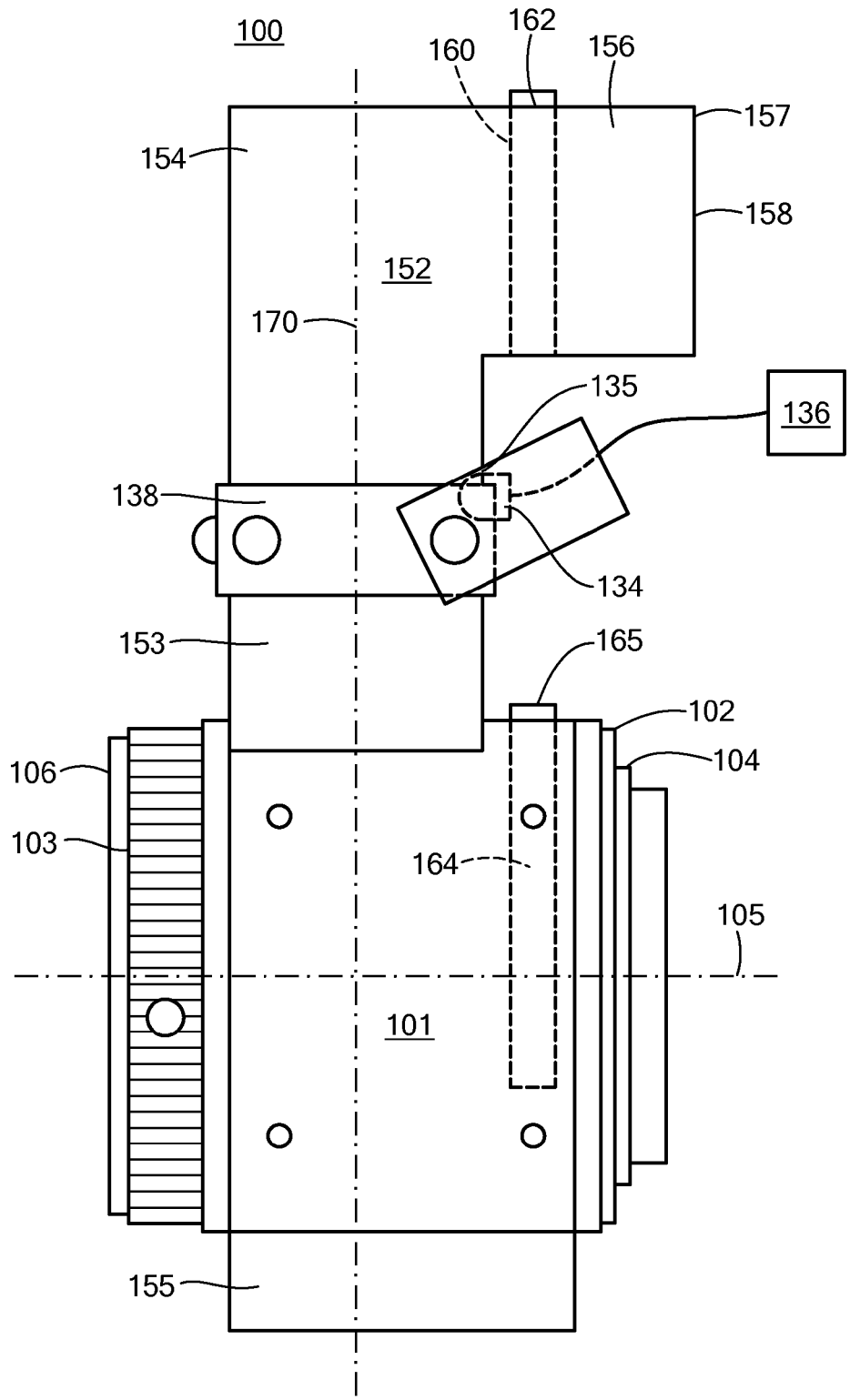
FIG. 2 is a side view of the adaptor of FIG. 1.
Figure 3:
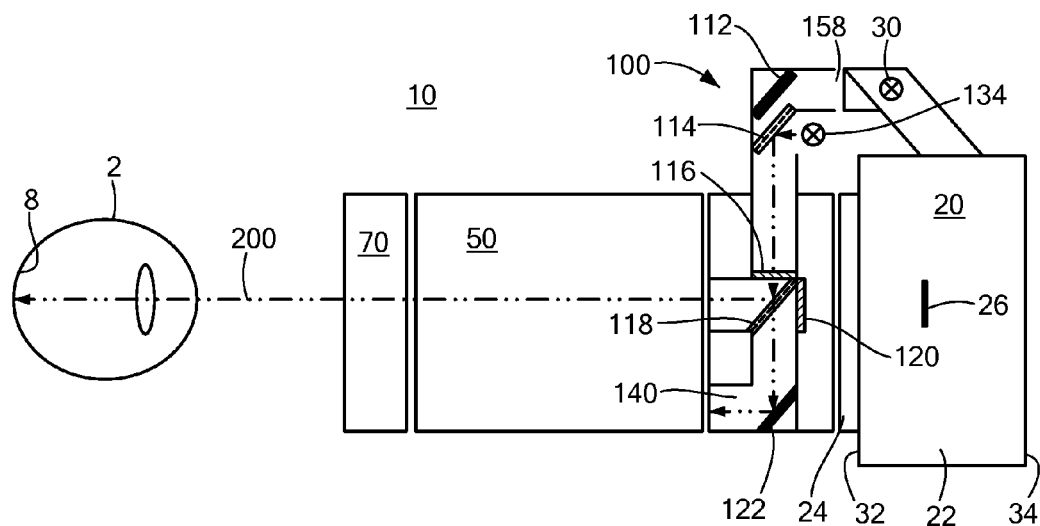
FIG. 3 is a schematic view of the first optical pathway of the device of FIG. 1.

Referring to FIGS. 1-3, an ophthalmic viewing and imaging device 10 includes a camera 20, and an adaptor 100. The camera 20 is a dSLR camera and includes a camera body 22 and a detachable camera lens 50. The adaptor 100 is mounted to the camera 20 between the camera body 22 and the camera lens 50, and includes optical components arranged to allow detailed viewing and imaging, with particular application to structures of the eye 2. Furthermore, use of the adaptor 100 in conjunction with a standard indirect ophthalmic lens 70 mounted to the camera lens 50 permits viewing and imaging of the posterior aspect (fundus) of the eye 2 as discussed further below. Here, "eye" refers to the eye of an animal, where the term animal is used here to include both human and non-human animals.

The camera body 22 is a Canon Rebel® XTi model by Canon U.S.A., Inc. of Lake Success, N.Y., although the device 10 is not limited to this model. The camera body 22 includes rear surface 34 which faces a user during use, and a front surface 32 opposed to the rear surface 34 and generally directed toward the viewed subject. A lens mount 24 is provided on the front surface 32, and a view finder (not shown) and LCD display (not shown) are provided on the rear surface 34. A CMOS image sensor 26 (FIG. 3, here a 22.2×14.8 mm detector) is disposed inside the camera body 22, and provides an effective 10.1 megapixel image resolution. The camera body 22 also includes a pop-up flash 30 having a guide number of at least 20 in feet for an ISO 100. In the illustrated embodiment, the camera flash 30 has a guide number of 43 in feet for an ISO 100, and recycle time of approximately 3 seconds. In addition, selection of camera shutter speed, aperture, ISO setting, single or video image, and other conventional features are easily set using switches (not shown) provided on the camera body 22.

The camera lens 50 is a standard fixed focal length macro lens such as an EF-S 60 mm/f2.8 lens by Canon U.S.A., Inc. of Lake Success, N.Y. The camera lens 50 includes a first end 62 having a lens mount interface 54. In conventional applications, the interface 54 permits the camera lens 50 to mount to the camera body 22, and is designed to cooperate with the lens mount 24 of the camera body 22 for this purpose. However, when used in the device 10, the interface 54 is used to connect the lens 50 to a corresponding interface 106 on the adaptor 100. Placement of the adaptor 100 between the camera lens 50 and the camera body 22 is advantageous since it results in a relatively forward placement of the camera lens 50 relative to the camera body 22. This creates a shorter working distance between the examiner and the patient (sometimes helpful in veterinary applications), and also increases image magnification. In addition, the camera lens 50 includes a second end 64 having a filter mounting thread 56 which permits ancillary devices such as filters or secondary lenses to be connected to the lens second end 64. In the embodiment shown in FIG. 1, the indirect ophthalmic lens 70 is secured to the lens second end 64. A focusing ring 58 is disposed between the first end 62 and the second end 64 of the lens 50.

The standard indirect ophthalmic lens 70 is an approximately 27 D lens having a magnification of 2.79× such as found in a Volk® Digital Clear Field model VDGTLCF provided by Volk Optical Inc., of Mentor, Ohio. The indirect ophthalmic lens includes a first end 72 having a lens mount interface 74, through which it is engaged to the corresponding mounting thread 56 provided on the second end 64 of the camera lens 50. By mounting the indirect ophthalmic lens 70 to the camera lens 50, the image seen at the camera detector 26 is an upright image (virtual image), whereby usability of the viewing device 10 is improved.

In the device 10, the adaptor 100 is disposed between the camera body 22 and the camera lens 50 and provides illumination of the interior of the eye 2 while it is being viewed and imaged through the device 10. The device 10 is particularly advantageous for illuminating, viewing, and imaging the fundus 8 of the eye 2. The adaptor 100 is configured to provide illumination of the fundus 8 at a relatively low intensity during visual examination, and also to provide illumination of the fundus 8 at a relatively high intensity during image acquisition. Finally, the adaptor 100 is configured to receive band pass (interference) filters to permit optional angiography of the fundus 8 using the device 10.

The adaptor 100 includes a generally cylindrical adaptor body 101 and an adaptor tube 152 which extends through the adaptor body 101.

The adaptor body 101 has a hollow cylindrical shape and includes a first end 102, a second end 103 that is opposed to the first end 102, and a longitudinal axis 105 that extends between the first and second ends 102, 103 along the centerline of the cylindrical body 101. A first connector 104 is disposed on the first end 102, and a second connector 106 is disposed on the second end 103. The first connector 104 is a lens mount configured to permit the adaptor 100 to be connected to the corresponding lens mount 24 provided on the camera body 22. When the adaptor body 101 is connected to the camera body 22 via the first connector 104, the adaptor longitudinal axis 105 is aligned with the optical axis 38 of the camera 20. The second connector 106 is also a lens mount, and is configured to permit a standard camera lens 50 to be connected to the second end 103 of the adaptor body 101 in such a way that the optical axis 66 of the camera lens 50 is aligned with both the adaptor longitudinal axis 105 and the optical axis of the camera 20. The first and second connectors 104, 106 also preserve the connections between the camera body 22 and the camera lens 50 required to maintain automatic focus and aperture control of the camera lens 50 by the camera 20.

The adaptor tube 152 has a hollow rectangular shape that includes a long portion 153 that extends outward from opposed sides of the adaptor body 101 in a direction generally transverse to the adaptor longitudinal axis 105 along a tube axis 170. A short portion 156 extends from a first end 154 of the long portion 153 in a direction generally parallel to the adaptor longitudinal axis 105. The respective interior spaces of the long and short portions 153, 156 are intersecting and thus form a continuous channel through which illumination is directed within the adaptor 100. The interior surface of the adaptor tube 152, as well as that of the adaptor body 101, is coated with a black matte finish so as to minimize unwanted reflections. In some embodiments, at least portions of the interior surface may be coated with a black fabric, such as a felt or velvet, for the same reason. A second end 155 of the long portion 153 resides on the opposed side of the adaptor body 101 relative to the first end 154. Due to its rectangular peripheral shape, the second end 155 of the long portion 153 serves, among other things, as a foot on which the adaptor 100 rests when placed on a flat support surface. As seen in FIG. 1, when the adaptor 100 is mounted between the camera body 22 and the camera lens 50, the second end 155 of the long portion 153 can also stabilize and support the viewing and imaging device 10 when placed on a flat support surface.

The terminal end 157 of the short portion 156 of the adaptor tube 152 is provided with an opening 158 through which light from an external flash enters the adaptor 100. In the illustrated embodiment, the opening 158 is open and defined by the sidewalls of the short portion 156. However, it is also contemplated that the terminal end 157 can be closed with a protective transparent cover to prevent dust and debris from entering the interior space of the adaptor 100. In order to maximize the amount of light captured from the camera flash 30, the distance between the short portion 156 of the adaptor tube 152 and the adaptor longitudinal axis 105 is determined by, and corresponds to, the height of the camera pop-up flash 30 when it is in it's extended operating position (as shown in FIG. 1). In addition, the axial length of the short portion 156 is sufficient to place the terminal end 157 at a location that is minimally spaced from the camera flash 30.

The long portion 153 of the adaptor tube 152 supports a single light emitting diode (LED) 134. The LED 134 extends through an opening 135 in the camera body-facing sidewall of the long portion 153 at a location between the adaptor body 101 and the short portion 156. A strap 138 secured to the outer surface of the tube 152 helps to support the LED 134 within the opening 135. The LED 134 is connected to and powered by an external power supply and controller 136. The single LED 134 provides a low level of continuous illumination, where "low" is used here as relative to the level of illumination provided by the camera flash 30. In particular, use of the single LED 134 provides a level of illumination that is, at maximum, sufficient to identify structures of interest within an interior of an eye, while minimizing discomfort of the patient during illumination. For example, in the illustrated embodiment, the LED 134 is Neutral White in color and provides 180 lumens at 700 mA. Use of a low level of illumination during observation is especially advantageous in veterinary settings where it can be difficult to maintain the patient's eye in the open position required for examination.

Referring to FIG. 3, the viewing and imaging device 10 includes several optical components which are arranged to direct light along a first optical pathway 200 (shown in dash-double dot lines) from the LED 134 through the adaptor 100, camera lens 50, and indirect ophthalmic lens 70 to the eye 2 for purposes of observation and examination of the fundus 8 of the eye 2 under low light conditions.

The first optical pathway 200 includes a first beam splitter 114 disposed in the adaptor tube long portion 153 at a location adjacent the LED 134. The first beam splitter 114 is a 30R/70T beam splitter and is oriented at 45 degrees relative to the tube axis 170, and thus directs 30 percent of the light emitted from the LED 134 toward the adaptor longitudinal axis 105. The first optical pathway 200 includes a second beam splitter 118 disposed in the adaptor tube long portion 153 at a location corresponding to the intersections of the tube axis 170 and the adaptor longitudinal axis 105, and a polarizing lens 116 disposed between the first and second beam splitters 114, 118. The second beam splitter 118 is a 50R/50T beam splitter and is oriented at 45 degrees relative to tube axis 170, and thus directs 50 percent of the light emitted from the first beam splitter 114 and polarized by the polarizing lens 116 along the adaptor longitudinal axis 105 toward the eye 2. In particular, the first optical pathway extends from the tube axis 170 through the camera lens 50 and the indirect ophthalmic lens 70 which together focus the light onto the fundus 8 of the eye 2. Focus of the image being viewed is adjusted by rotation of the focus ring 58 provided on the camera lens 50, and/or by adjustment of the distance between the device 10 and the subject.

Figure 4:
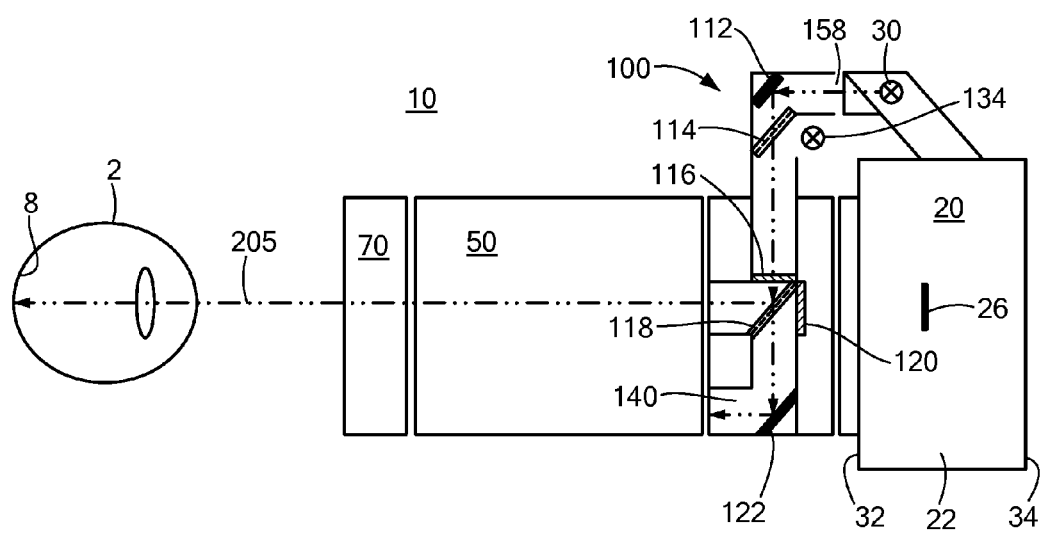
FIG. 4 is a schematic view of the second optical pathway of the device of FIG. 1.

Referring to FIG. 4, the viewing and imaging device 10 includes several optical components which are arranged to direct light along a second optical pathway 205 (shown in dashed lines) from an external light source such as the camera flash 30 through the adaptor 100, camera lens 50 and indirect ophthalmic lens 70 to the fundus 8 of the eye 2 for purposes of obtaining an image of fundus 8.

The second optical pathway 205 includes a mirror 112 disposed in the adaptor tube long portion at a location corresponding to the first end 154 of the tube long portion 153. The mirror 112 is oriented at 45 degrees relative to the tube axis, and thus directs light received from the camera flash 30 along the tube axis 170 toward the adaptor body 101. The light transmitted from the mirror 112 passes through the first beam splitter 114, which is disposed in the adaptor tube long portion 153 at a location adjacent the LED 134. Here, 70 percent of the light emitted from the camera flash 30 is transmitted through the first beam splitter 114 and directed through the polarizing lens 116 toward the second beam splitter 118. Since the second beam splitter 118 is a 50R/50T beam splitter, 50 percent of the light emitted from the first beam splitter 114 and polarized by the polarizing lens 116 is transmitted along the adaptor longitudinal axis 105 toward the eye 2.

In both the first and second optical pathways 200, 205, there is a portion of the light that is not reflected, but is instead transmitted through the second beam splitter 118. The transmitted portion travels along tube axis 170 toward a mirror 122 disposed within the second end 155 of the tube long portion 153. The mirror 122 is also oriented at 45 degrees relative to the tube axis 170, whereby the portion is reflected away from the camera body 22 and into a light trap 140.

The viewing and imaging device advantageously uses the camera pop up flash 30 to provide the illumination required for obtaining images of the fundus 8. Prior to obtaining an image, focusing is performed by rotation of the focus ring 58 of the camera lens 50 and/or by adjusting the spacing between the device 10 and the eye 2. Once the image is in focus, an image is obtained by simply pressing the shutter button of the camera 20. Appropriate exposure is obtained since the camera flash 30 is triggered using the camera shutter button, and flash duration is controlled by through the lens (TTL) metering.

Note that only 70 percent of the light emitted by the camera flash 30 is transmitted from the camera flash 30 to the second beam splitter 118, and only 50 percent of that light is transmitted to the eye. However, the light transmitted to the eye 2 along the second optical pathway 205 is much greater than that transmitted along the first optical pathway 200, due to the large difference between the amount of light emitted from the camera flash 30 and from the LED 134. In this regard, in order to obtain even greater illumination along the second optical pathway and/or shorter flash recycle times, an external light source other than the camera flash 30 can be used to transmit light into the opening 158 of the adaptor tube 152.

Figure 5:
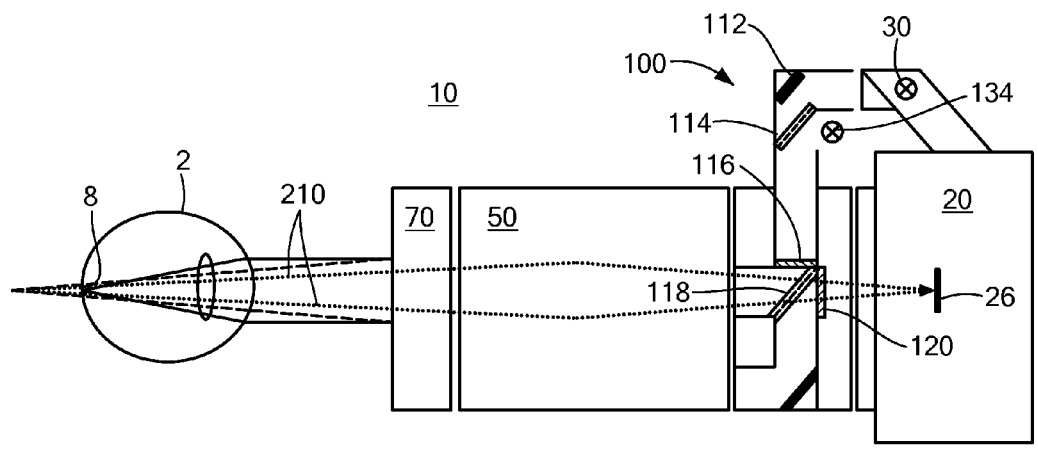
FIG. 5 is a schematic view of the third optical pathway of the device of FIG. 1.

Referring to FIG. 5, the viewing and imaging device 10 also includes a third optical pathway 210 (shown by dotted lines) to direct light reflected from the fundus 8 of the eye 2 to the camera detector 26. The third optical pathway includes the indirect ophthalmic lens 70 and the camera lens 50 which focus the reflected light back to the adaptor 100, where it passes through the second beam splitter 118, and a second polarizing lens 120 before being detected by the camera detector 26. The second polarizing lens 120 is identical to the first polarizing lens 116, but is oriented so that the polarization directions of the first and second polarizing filters 116, 120 are transverse to each other. This arrangement minimizes transmittal of unwanted reflections to the camera detector 26.

Each of the first, second and third optical pathways 200, 205, 210 includes at least a portion that is coincident with the optical axis of the camera 20 and the longitudinal axis of the adaptor 100. Thus, use of the adaptor 100 with the camera 20 provides true coaxial illumination during viewing and image acquisition.

Figure 6:
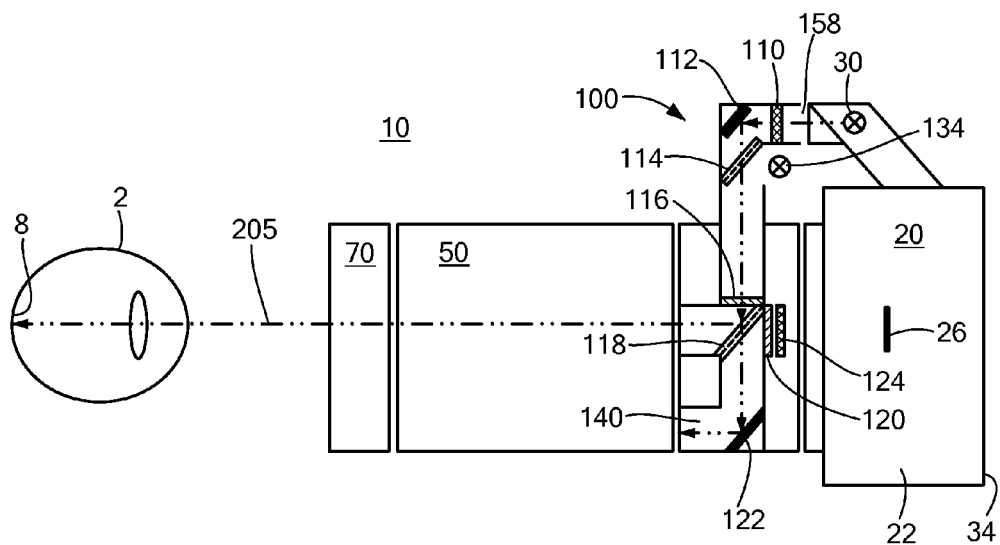
FIG. 6 is a schematic view of the second optical pathway of the device of FIG. 1 including optional optical components used for fluorescein angiography.
Figure 7:
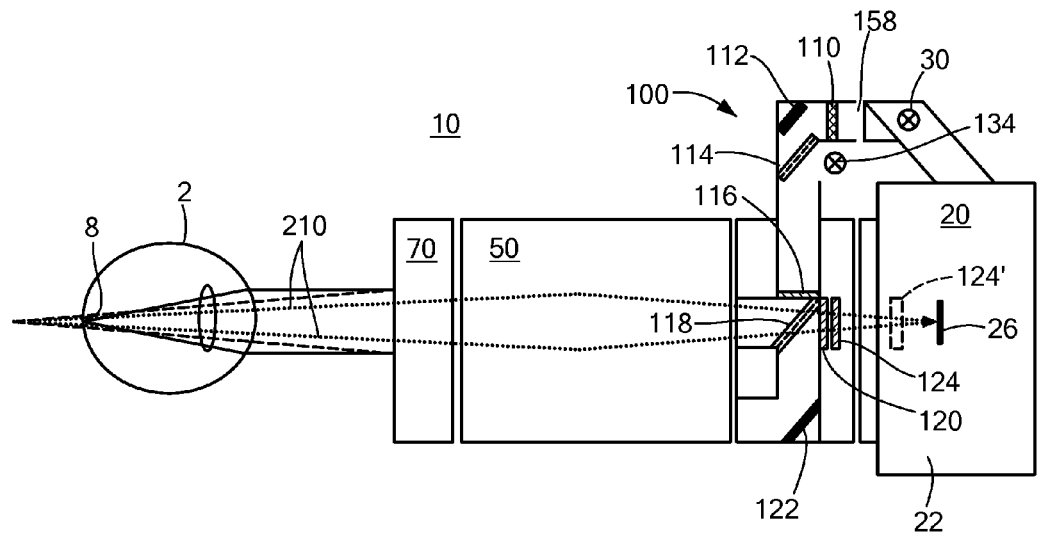
FIG. 7 is a schematic view of the third optical pathway of the device of FIG. 1 including optional optical components used for fluorescein angiography.

Referring to FIGS. 2, 6 and 7, the device 10 can be used to perform fluorescein angiography of the fundus 8. To enable this optional function, the adaptor 100 is configured to permit selective insertion and withdrawal of additional optical components therewithin. In particular, the adaptor short portion 156 is formed having a slot 160 dimensioned to receive and support a first band pass filter 110. The slot 160 is positioned to place the first band pass filter 110 within the second optical pathway 205 at a location between the opening 158 and the first mirror 112 (FIGS. 2 and 6). The slot 160 is normally covered by a removable slot cover 162 to prevent unwanted illumination, as well as dust and debris, from entering the adaptor short portion 156. Similarly, the adaptor body 101 is formed having a slot 164 dimensioned to receive and support a second band pass filter 124. The slot 164 is positioned to place the second band pass filter 124 within the third optical pathway 210 at a location between the second polarization filter 120 and the camera detector 26 (FIGS. 2 and 7). The slot 164 is normally covered by a removable slot cover 165 to prevent unwanted illumination, as well as dust and debris, from entering the adaptor body 101. Thus, the first and second band pass filters 110, 124 can be easily inserted in and/or removed from the adaptor 100 as needed.

In order to enable stimulation of fluorescein previously administered to the patient, the first band pass filter 110 is selected to permit transmission of light of an appropriate wavelength. For example, the first band pass filter 110 can have a transmission wavelength in a range of 485 nm to 500 nm. In the illustrated embodiment, the first band pass filter 110 transmits light having a wavelength of 485 nm along the second optical pathway 205. In order to enable an image to be obtained of the stimulated fluorescein within the fundus, the second band pass filter 124 is selected to permit transmission of an appropriate wavelength. For example, the second band pass filter 124 transmits light having a wavelength in a range of 520 nm to 630 nm. In the illustrated embodiment, the second band pass filter 124 transmits light having a wavelength of 532 nm.

In an alternative arrangement, indocyanine green angiography can be performed by appropriate replacement of the first band pass filter 110, along with minimal modification of the camera 20. In order to enable stimulation of indocyanine green previously administered to the patient, the first band pass filter 110 is selected to permit transmission of light of an appropriate wavelength. For example, the first band pass filter can have a transmission wavelength in a range of 770 nm to 810 nm. In the illustrated embodiment, the first band pass filter 110 transmits light having a wavelength of 800 nm.

In order to enable image capture of the stimulated indocyanine green, the second band pass filter 124 is omitted, and a modified camera is used. In the modified camera, a low pass filter normally positioned in front of the camera detector 26 is replaced with an appropriate replacement band pass filter 124'. For example, the replacement band pass filter 124' can have a transmission wavelength in a range of 820 nm to 850 nm in order to transmit light resulting from the stimulated indocyanine green within the fundus 8. In the illustrated embodiment, the replacement band pass filter 124' transmits light having a wavelength of 820 nm, whereby indocyanine green angiography can be performed.

Figure 8:
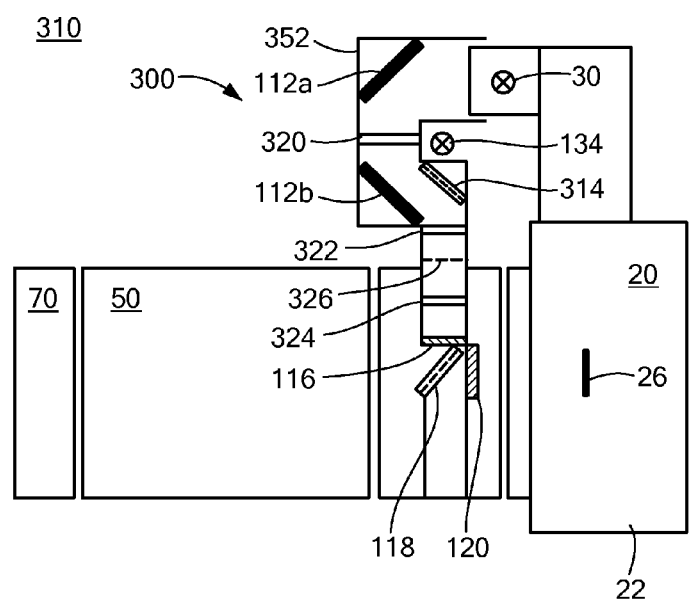
FIG. 8 is a schematic view of an ophthalmic viewing and imaging device including a first alternative embodiment of the adaptor of FIG. 1.

Referring to FIG. 8, an alternative embodiment viewing and imaging device 310 includes a modified adaptor 300 including an alternative arrangement of optical components within the modified adaptor 300. For example, to accommodate variations in the design of the camera pop up flash 30, which varies from camera to camera, the adaptor tube 152 can be replaced with an adaptor tube 352 of modified shape. For example, in the illustrated embodiment, the adaptor tube 352 is generally hook-shaped, and includes two mirrors 112a, 112b to direct light as required. In addition, the first beam splitter 314 has different reflectance and transmittance properties relative to the first beam splitter 114 of the previous embodiment. In particular, the first beam splitter 314 is a 70R/30T beam splitter so as to maximize light transmitted from the camera flash 30.

The modified adaptor 300 may optionally further include condensing lenses 320, 322, 324 to maximize transmission of light from the light sources 134, 30 toward the eye 2. For example, a first condensing lens 320 may be provided in front of the camera flash 30, between the two mirrors 112a, 112b, and will collect the light emitted from the camera flash 30 and cause it to become convergent, such that its focus is at the first beam splitter 314. A second condensing lens 322 is placed following the LED 134, such that the focal point of the second condensing lens 322 is at the first beam splitter 314. This arrangement results in the light being collected from the LED 134 (which will be divergent) and the light from the first condensing lens 320 (i.e. the camera flash 30) which will also now be divergent. After passing through this condensing lens, these rays will now be parallel. A third condensing lens 324 is located just before the first polarizing filter 116. The third condensing lens 324 will receive the parallel rays and converge them with a focal point at the second beam splitter 118. Light reflected by the second beam splitter 118 will then become divergent, with the size of the light cone formed at the camera lens 50 matching the size of its inside lens. Also, between the last two lenses, a diaphragm 326 may be employed to control the level of illumination of the passing parallel rays. The diaphragm 326 will ultimately control the size of the light cone entering into the camera lens 50, and needs to be considered when altering the size of the aperture on the camera lens 50.

Figure 9:
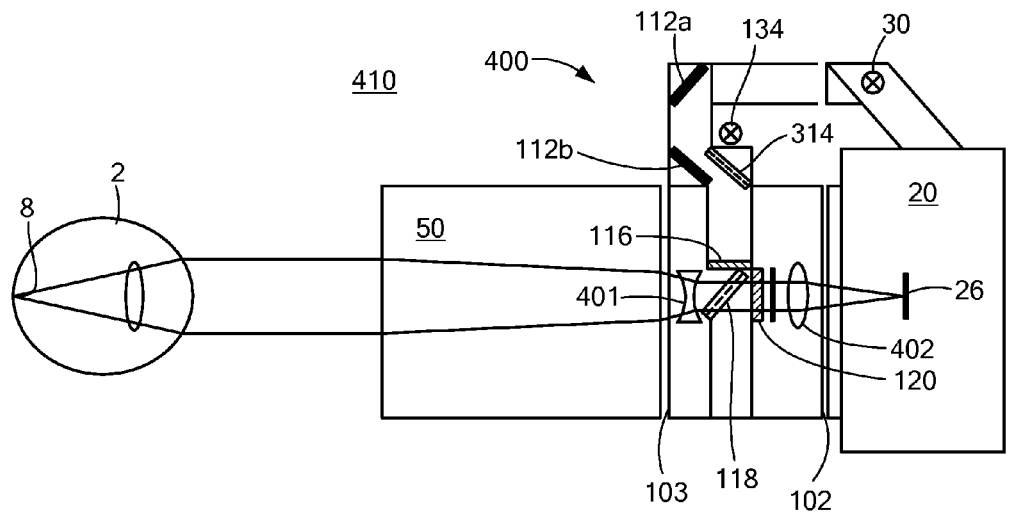
FIG. 9 is a schematic view of an ophthalmic viewing and imaging device including a second alternative embodiment of the adaptor of FIG. 1.

Referring to FIG. 9, another alternative embodiment viewing and imaging device 410 includes a modified adaptor 400 that includes additional lenses 401, 402 to enhance transmission of light from the eye 2 toward the camera detector 26. In this embodiment, a divergent lens 401 (double concave (shown) or plano concave) is positioned between the adaptor second end 103 and the second beam splitter 118. In addition, a convergent lens 402 (double convex (shown) or plano convex) is positioned between the second polarizing filter 120 and the adaptor first end 102. The divergent lens 401 serves to make the rays from the camera lens parallel, and the convergent lens 402 receives the parallel rays and focuses them onto the camera sensor 26. This configuration advantageously provides normal upright imaging without requiring use of the indirect ophthalmic lens 70. However, fundus viewing is inverted. Of course this inversion can be corrected by further simple insertion of an inverter (two prisms perpendicular to each other, not shown).

Figure 10:
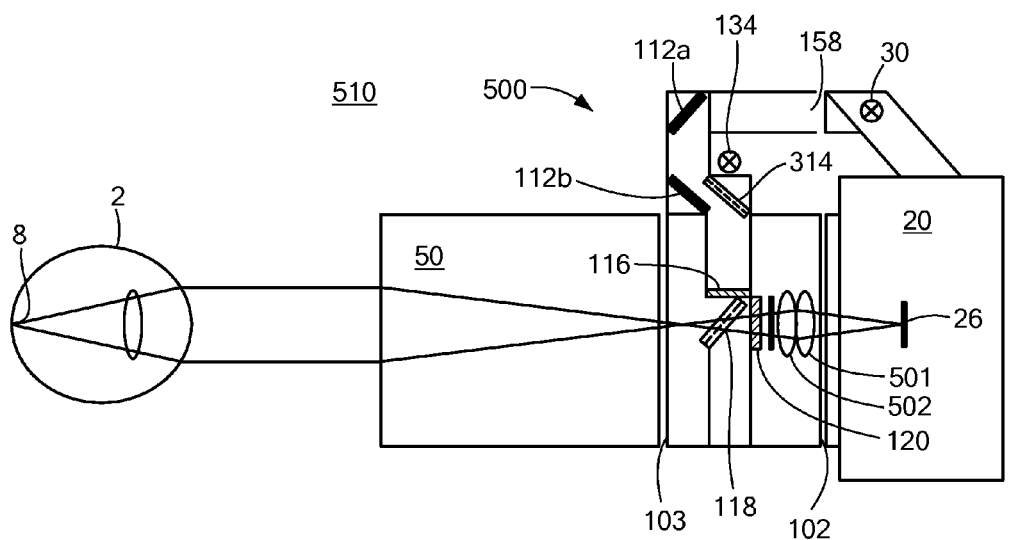
FIG. 10 is a schematic view of an ophthalmic viewing and imaging device including a third alternative embodiment of the adaptor of FIG. 1.

Referring to FIG. 10, still another alternative embodiment viewing and imaging device 510 includes a modified 500 adaptor that, like the previous embodiment adaptor 400, includes additional lenses to enhance transmission of light toward the camera detector 26. The modified adaptor 500 includes two convergent lenses 501, 502 (double convex (shown) or plano convex) that are positioned between the second polarizing filter 120 and the adaptor first end 102. The two convergent lenses 501, 502 are positioned so that their focal lengths are matched to the distances between the image formed by the camera lens 50 and the camera sensor 26. By using this configuration, the indirect lens 70 is not required because the ability for focusing at infinity, lost under the conditions shown in FIG. 3, is regained. In addition, the fundus image received would be viewed as an upright image for the examiner (the image would be inverted by viewing of the fundus and it would be inverted again within the adaptor). However, the image would only be upright when viewing the fundus, and would be upside down for everything else. Of course, the same benefits can be obtained by use of a single converging (positive) lens that it is placed 2 focal lengths between both the image formed by the camera lens (in the case of the illustrated camera lens 50, this is 44 mm behind it) and the camera sensor 26. However, using two lenses 501, 502 as shown in the figure, as opposed to one, shortens the overall distance and the length of the adaptor.

Figure 11:
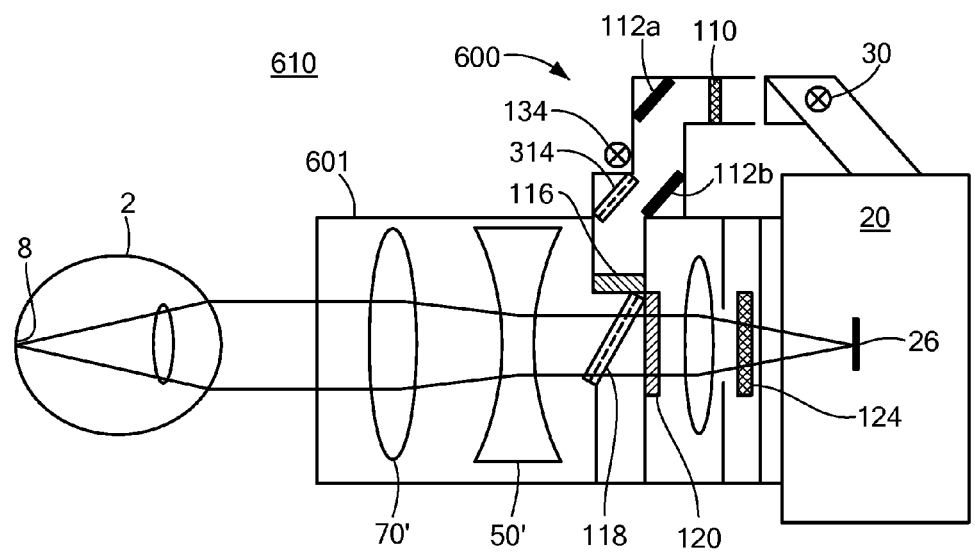
FIG. 11 is a schematic view of an ophthalmic viewing and imaging device including a fourth alternative embodiment of the adaptor of FIG. 1.

Referring to FIG. 11, another alternative embodiment viewing and imaging device 610 includes an adaptor 600 that incorporates the lenses previously provided by the camera lens 50 and the indirect ophthalmic lens 70 (schematically shown as 50' and 70', respectively) into the adaptor body 601. Thus, in this embodiment, the adaptor 600 provides a single functional unit that mounts directly to the camera body 22, provides coaxial illumination of the viewed object, and in which the camera lens 50 and indirect ophthalmic lens are omitted.

Figure 12:
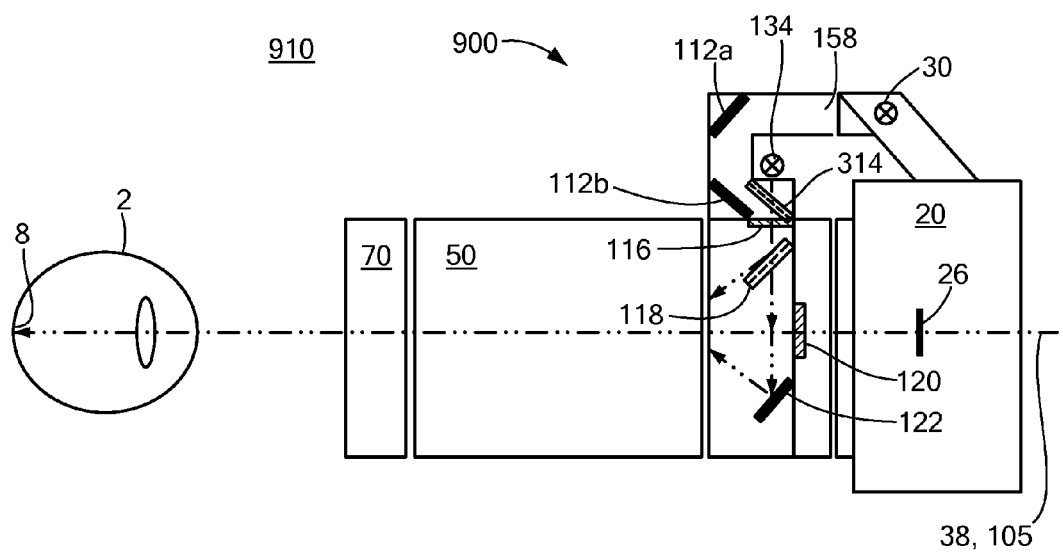
FIG. 12 is a schematic view of an ophthalmic viewing and imaging device including a fifth alternative embodiment of the adaptor of FIG. 1.

Referring to FIG. 12, another alternative embodiment viewing and imaging device 910 includes an adaptor 900 in which first polarizing filter 116 and the second beam splitter 118 are moved away from the adaptor axis 105 (which is coincident with the camera axis 38) to a location between the LED 134 and the adaptor axis 105. In addition, the second mirror 122 is moved to a location closer to the adaptor axis 105 so that it is disposed between the adaptor tube second end 155 and the adaptor axis 105. In this configuration light reflected from the second beam splitter 118 is directed toward the camera lens 50. In addition, the light transmitted through the second beam splitter 118 and then reflected from the second mirror 122 is also directed toward the camera lens 50.

Figure 13:
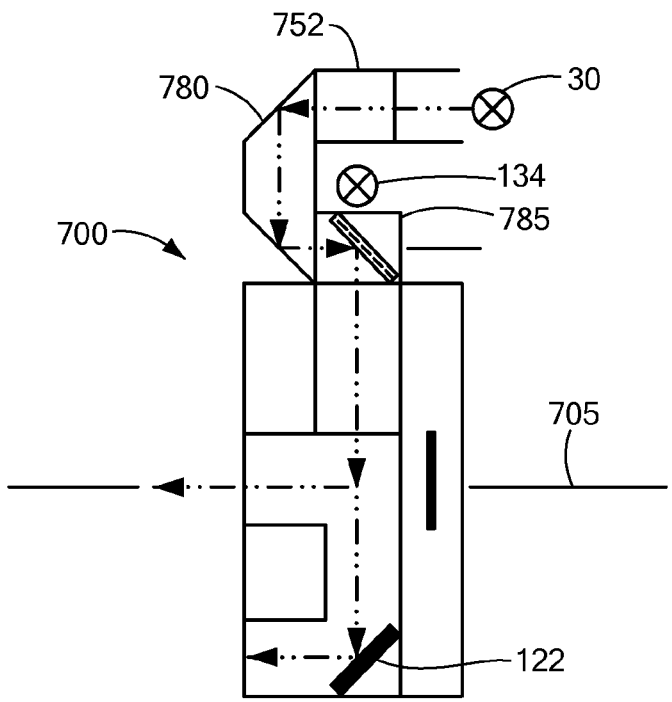
FIG. 13 is a schematic view of a sixth alternative embodiment of the adaptor of FIG. 1.
Figure 14:
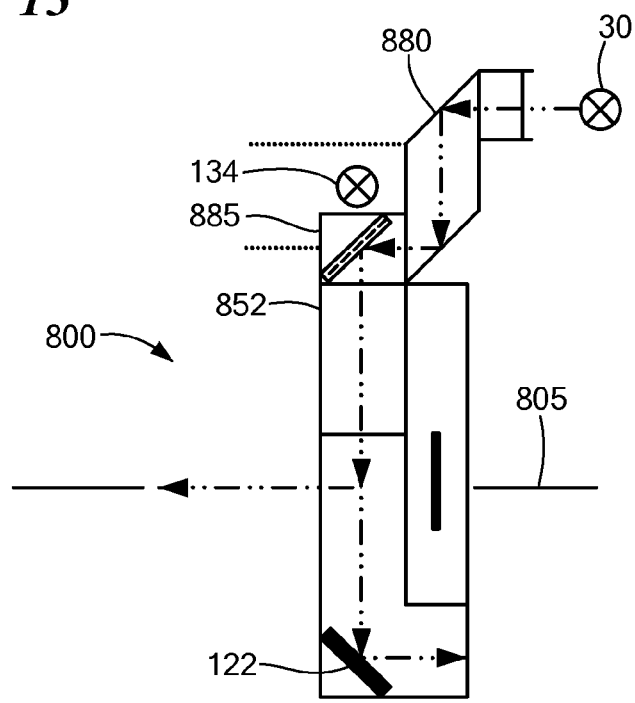
FIG. 14 is a schematic view of a seventh alternative embodiment of the adaptor of FIG. 1.

Referring to FIGS. 13 and 14, any of the above described adaptors 100, 300, 400, 500, 600, 900 may be further modified to replace mirrors with prisms to redirect light within the adaptor body 101 and tube 152. Although of higher cost than mirrors, prisms are advantageous due to the increased alignment accuracy and quality control that they afford. As seen in FIG. 13, an alternative adaptor 700 includes a dove prism 780 positioned within the adaptor tube 752 at a location to receive light from the camera flash 30 and direct it to a cube beam splitter 785. Like the first beam splitter 314, the cube beam splitter 785 is a 70R/30T beam splitter and is oriented so as to direct 70 percent of the light emitted from the camera flash 30 toward the adaptor longitudinal axis 705, and 30 percent of the light emitted from the LED 134 toward the adaptor longitudinal axis 705. As seen in FIG. 14, an alternative adaptor 800 includes a rhomboid prism 880 positioned within the adaptor tube 852 at a location to receive light from the camera flash 30 and direct it to a cube beam splitter 885. The cube beam splitter 885 is a 70R/30T beam splitter and is oriented at 45 degrees relative to the tube axis so as to direct 70 percent of the light emitted from the camera flash 30 and 30 percent of the light emitted from the LED 134 toward the adaptor longitudinal axis 805.

Although disclosed herein as an ophthalmic viewing and imaging device, the device is not limited to ophthalmic imaging, and its use can be extended to standard close up photography and macro-photography, particularly when used without the indirect ophthalmic lens.

Although the illustrated embodiment employs a Canon Rebel® XTi dSLR camera and an EF-S 60 mm/F2.8 macro lens, the viewing device is not limited to these particular components. The adaptor can be used with any conventional SLR camera (digital and non-digital) and lens with appropriate modification of the adaptor connector portions 104, 106.

Figure 15:
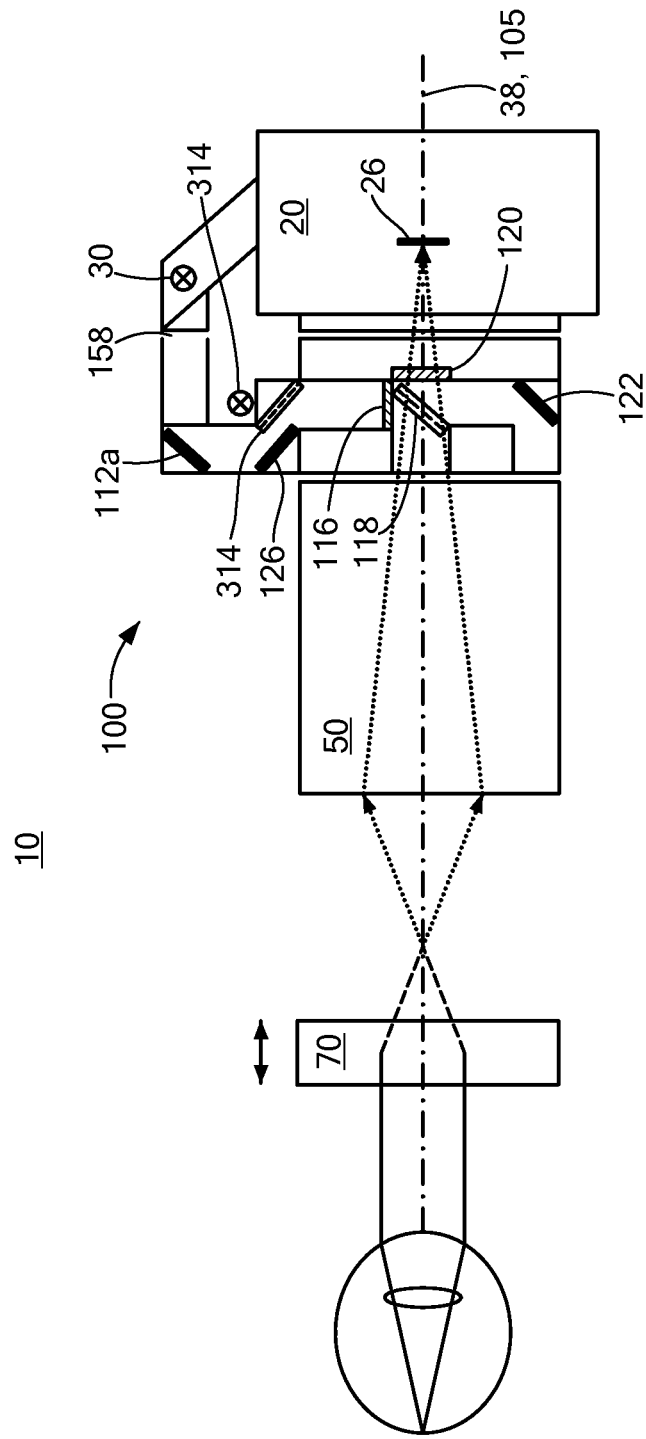
FIG. 15 is a schematic view of the ophthalmic viewing and imaging device of FIG. 8 illustrating axial positioning (represented by double headed arrow) of the indirect ophthalmic lens.

Referring to FIG. 15, although the illustrated embodiments employ a standard indirect ophthalmic lens, the viewing device is not limited to use of this lens. For example, substitution of a different lens at this location permits modification of the working distance and field of view. However, depending on the diopter and working distance of the substituted lens, such substitution may result in additional lenses being required between the indirect lens 70 and the camera lens 50. In addition, rather than being fixed to the mounting thread 56 of the camera lens 50, the indirect lens 70 can be detached from the camera lens second end 64 and moved (for example, manually) along the camera axis 38. This may be required based on the specifications of the lenses 50, 70 being used and the final working distance of the camera lens 50 once it connected to the adaptor 100. Also, forward movement of the indirect lens 70 along the camera axis 38 such that its focal point is at the focal plane of the camera 20, would allow for a real image (i.e., an image that is upside down and backwards) to be formed. This may be advantageous to some users as it is a more common method of viewing the fundus 8. Moreover, because the indirect ophthalmic lens 70 is a separate component from the adaptor 100, device 10 can be used without the indirect ophthalmic lens 70 to view and image non-ophthalmic subjects and can perform standard close-up and macrophotography.

In some embodiments, the view and imaging device 10 may include additional optical components. For example, an anti-reflection filter (not shown) may be provided in the adaptor 100 between the second band pass filter 118 and the camera lens 50 to further reduce unwanted reflections within the device. At this location, the filter will affect each of the first, second and third optical pathways 200, 205, 210.

Although the illustrated embodiment shows the LED as powered by an external power supply 136, the invention is not limited thereto. For example, the power supply can be included within the adaptor body 101. Alternatively, the LED can be powered by the battery located within the camera body 22.

Although the illustrated embodiment uses a 50R/50T beam splitter as the second beam splitter 118, the adaptor is not limited to this configuration. For example, in some embodiments, the second beam splitter 118 can be replaced with a holed mirror. This modification minimizes loss of the returning light that is transmitted from the eye 2 to the camera detector 26.

Advantages of the viewing and imaging device disclosed herein include its versatility, portability and cost. This device provides not only high resolution digital fundus images, but additionally provides fluorescein and indocyanine green angiography capabilities and offers a significant benefit to the medical profession. These imaging modalities are often limited in their availability due to the cost of conventional equipment. Furthermore, the compact size and light weight of the device allows it to be easily handled and transported to remote locations (i.e. bed side evaluation, remote satellite clinic.

What is claimed is:

1. An adaptor configured to adapt a camera for use as an ophthalmic viewing and imaging device, the adaptor comprising
    a body including a first interface configured to connect to the camera so that an optical axis of the adaptor is aligned with an optical axis of the camera and a second interface configured to connect to a camera lens so that the optical axis of the adaptor is aligned with an optical axis of the camera lens,
    a first light source disposed within the body and configured to provide a level of illumination that is, at maximum, sufficient to identify structures of interest within an interior of an eye,
    a first optical pathway for directing light from the first light source to the camera lens,
    a second optical pathway for directing light from a second light source to the camera lens, the second light source disposed externally relative to the body, and
    a third optical pathway for directing light from the camera lens through the adaptor to the camera.

2. The adaptor of claim 1, wherein the first, second and third optical pathways each include a portion that is coincident with the optical axis of the camera.

3. The adaptor of claim 1, wherein the first light source includes a light emitting diode.

4. The adaptor of claim 1, wherein the adaptor further comprises the second light source, the second light source configured to provide a level of illumination that is, at minimum, sufficient to obtain images of the structures of interest.

5. The adaptor of claim 4, wherein the second light source includes a flash.

6. The adaptor of claim 1, wherein the adaptor further includes a band pass filter disposed in the second optical pathway.

7. The adaptor of claim 1, wherein the first optical pathway includes
    the first light source,
    a first beam splitter which directs a portion of the light emitted from the first light source to a second beam splitter, and
    the second beam splitter which directs a portion of the light received from the first beam splitter along the optical axis of the adapter in a direction toward the second interface.

8. The adaptor of claim 7, wherein the adaptor further includes a polarized filter disposed in the first optical pathway between the first and second beam splitters.

9. The adaptor of claim 8, wherein the third optical pathway includes a second polarizing filter, the second polarizing filter having an opposed orientation relative to the polarizing filter of the first optical pathway.

10. The adaptor of claim 7, wherein the adaptor further includes a mirror disposed so as to deflect light transmitted through the second beam splitter in a direction away from the first interface.

11. The adaptor of claim 7, wherein the third optical pathway includes the second beam splitter.

12. The adaptor of claim 1, wherein the second optical pathway includes
    a mirror which directs light emitted from the second light source toward a beam splitter, and
    a beam splitter which directs a portion of the light received from the mirror along the optical axis of the adapter in a direction toward the second interface.

13. The adaptor of claim 1, wherein the third optical pathway extends along the optical axis, and passes through each of the first and second interfaces.

14. The adaptor of claim 1, wherein the third optical pathway includes a band pass filter disposed between a polarizing filter and the first interface.

15. The adaptor of claim 14, wherein the third optical pathway includes a lens disposed between the band pass filter and the first interface.

16. The adaptor of claim 1, wherein the body includes
    a cylindrical base having longitudinal axis coincident with the optical axis of the adaptor, and
    a tube extending outward from a surface of the base and along an axis transverse to the optical axis of the adaptor.

17. An ophthalmic viewing and imaging device comprising
    a camera including a camera lens, and
    an adaptor connected to the camera so as to be disposed between the camera and the camera lens, the adaptor comprising
        a body including a first interface configured to connect to the camera so that an optical axis of the adaptor is aligned with an optical axis of the camera and a second interface configured to connect to the camera lens so that the optical axis of the adaptor is aligned with an optical axis of the camera lens,
        a first light source configured to provide a level of illumination that is, at maximum, sufficient to identify structures of interest within an interior of an eye,
        a first optical pathway for directing light from the first light source to the camera lens,
        a second optical pathway for directing light from a second light source to the camera lens, and
        a third optical pathway for directing light from the camera lens through the adaptor to the camera.

18. The device of claim 17, wherein the first, second and third optical pathways each include a portion that is coincident with the optical axis of the camera.

19. The device of claim 17, wherein the first light source includes a light emitting diode.

20. The device of claim 17, wherein the adaptor further includes a band pass filter disposed in the second optical pathway.

21. The device of claim 17, wherein the first optical pathway includes the first light source,
    a first beam splitter which directs a portion of the light emitted from the first light source to a second beam splitter, and
    the second beam splitter which directs a portion of the light received from the first beam splitter along the optical axis of the adapter in a direction toward the second interface.

22. The device of claim 21, wherein the first light source is a light emitting diode.

23. The device of claim 21, wherein the adaptor further includes a polarized filter disposed in the first optical pathway between the first and second beam splitters.

24. The device of claim 23, wherein the third optical pathway includes a second polarizing filter, the second polarizing filter having an opposed orientation relative to the polarizing filter of the first optical pathway.

25. The device of claim 21, wherein the adaptor further includes a mirror disposed so as to deflect light transmitted through the second beam splitter in a direction away from the first interface.

26. The device of claim 21, wherein the third optical pathway includes the second beam splitter.

27. The device of claim 17, wherein the second optical pathway includes
- a mirror which directs light emitted from the second light source toward a beam splitter, and
- a beam splitter which directs a portion of the light received from the mirror along the optical axis of the adapter in a direction toward the second interface.

28. The device of claim 17, further including a lens mounted to the camera lens on a side of the camera lens that is opposed to the adaptor.

29. The device of claim 17, wherein the third optical pathway includes a band pass filter disposed between the first interface and the camera image detector.

\* \* \* \* \*